(12) United States Patent
Liu

(10) Patent No.: US 10,513,049 B2
(45) Date of Patent: Dec. 24, 2019

(54) PUMP-TYPE AUTOCLAVE SYSTEM AND PROVIDING METHOD FOR STEAM AND PRESSURE THEREOF

(71) Applicant: Kai Liu, Shandong (CN)

(72) Inventor: Kai Liu, Shandong (CN)

(*) Notice: Subject to any disclaimer, the term of this patent is extended or adjusted under 35 U.S.C. 154(b) by 876 days.

(21) Appl. No.: 14/414,651

(22) PCT Filed: Nov. 2, 2014

(86) PCT No.: PCT/CN2014/071958
§ 371 (c)(1),
(2) Date: Jan. 13, 2015

(87) PCT Pub. No.: WO2015/120573
PCT Pub. Date: Aug. 20, 2015

(65) Prior Publication Data
US 2016/0368163 A1 Dec. 22, 2016

(51) Int. Cl.
*B28B 11/24* (2006.01)
*B01J 3/04* (2006.01)
(Continued)

(52) U.S. Cl.
CPC .............. *B28B 11/245* (2013.01); *B01J 3/04* (2013.01); *B28B 11/247* (2013.01); *F22B 1/006* (2013.01);
(Continued)

(58) Field of Classification Search
CPC ...... B28B 11/245; B28B 11/247; F22B 33/18; F24J 2/42; F24J 2/055
See application file for complete search history.

(56) References Cited

U.S. PATENT DOCUMENTS 3,672,009 A * 6/1972 Pike ........................... B01J 3/04
                                                             122/33
4,239,730 A * 12/1980 Fahlvik ..................... A61L 2/24
                                                             422/109
(Continued)

*Primary Examiner* — Galen H Hauth
(74) *Attorney, Agent, or Firm* — Houtteman Law LLC

(57) ABSTRACT

The present invention discloses a pump-type autoclave system and a providing method for steam and pressure thereof, wherein the pump-type autoclave system comprises an autoclave, a steam providing device and a compressor, said steam providing device comprises a water storage container and a heating device used for heating said water storage container, said water storage container, the compressor and the autoclave are connected through a pipeline to form a closed loop, an inlet of the compressor is connected with a steam output port of the water storage container, an outlet of the compressor is connected to a steam input port of the autoclave, and a condensate water drain outlet of the autoclave is connected to the water storage container. The present invention uses the compressor to depressurize an intermediate-low temperature water source to obtain steam, and the steam is pumped into the autoclave and condensed to release heat to obtain corresponding temperature and pressure. Since the present invention fully utilizes a great amount of low-cost intermediate-low temperature heat sources obtained from natural, industrial or living waste heat to provide needed high temperature, steam and pressure to the autoclave system, the energy is saved.

1 Claim, 1 Drawing Sheet

(51) Int. Cl.
*F22B 1/00* (2006.01)
*F22B 33/18* (2006.01)
*F24S 90/00* (2018.01)
*F24S 10/40* (2018.01)
*A61L 2/07* (2006.01)

(52) U.S. Cl.
CPC .............. *F22B 33/18* (2013.01); *F24S 10/45* (2018.05); *F24S 90/00* (2018.05); *A61L 2/07* (2013.01); *A61L 2202/11* (2013.01); *A61L 2202/14* (2013.01); *Y02E 10/44* (2013.01)

(56) References Cited

U.S. PATENT DOCUMENTS

| | | | | |
|---|---|---|---|---|
| 4,570,443 | A * | 2/1986 | Specht | B01J 3/002 |
| | | | | 422/242 |
| 2009/0056303 | A1 * | 3/2009 | Araki | F02C 7/1435 |
| | | | | 60/39.53 |

* cited by examiner

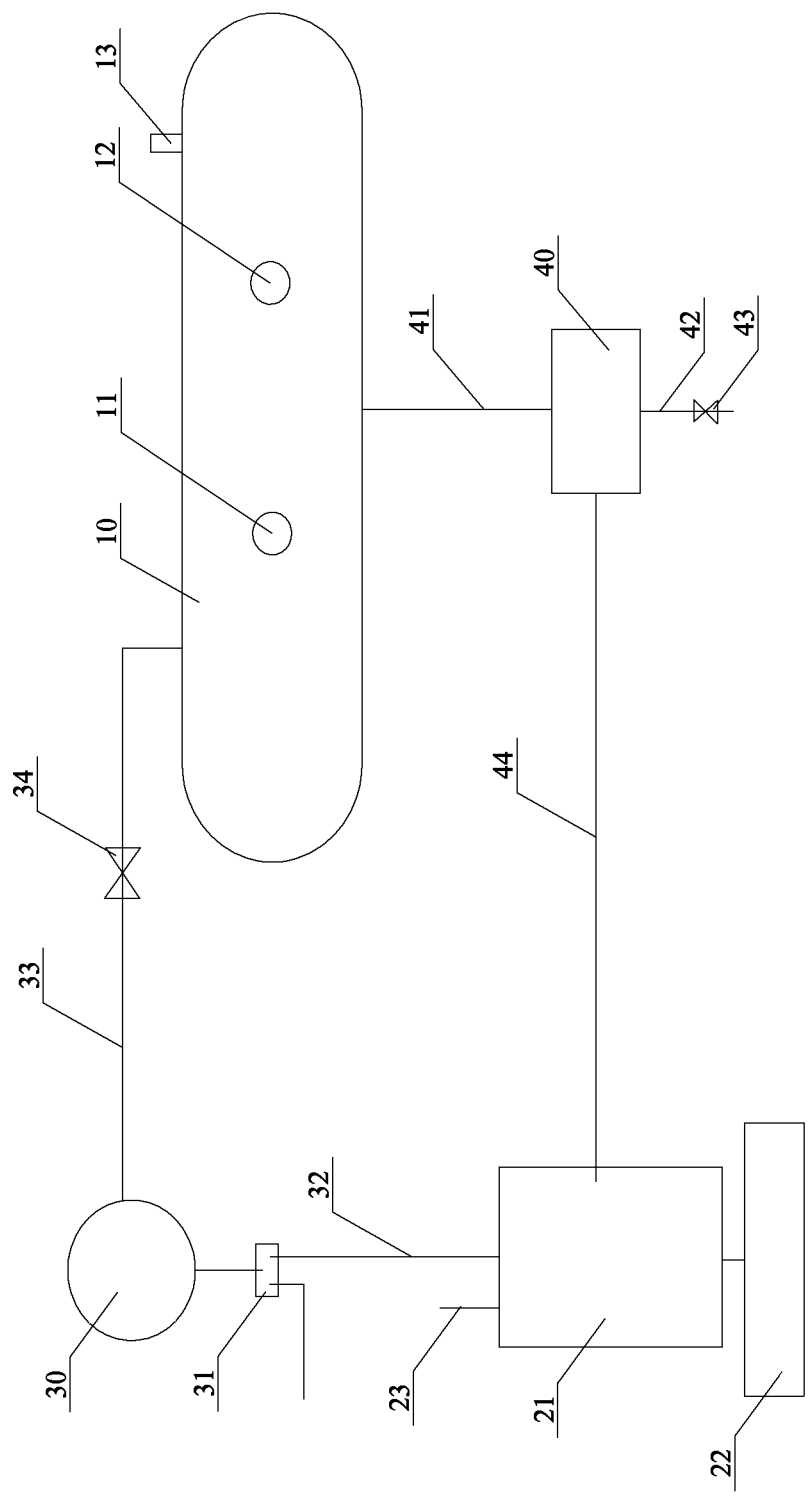

PUMP-TYPE AUTOCLAVE SYSTEM AND PROVIDING METHOD FOR STEAM AND PRESSURE THEREOF

FIELD OF THE INVENTION

The present invention relates to an autoclave system, in particular to a pump-type autoclave system and a providing method for steam and pressure thereof.

BACKGROUND OF THE INVENTION

An autoclave system mainly consists of an autoclave, a steam providing device and a safety control device, and the application thereof is very wide. The autoclave system is widely applied to autoclave curing of building materials such as aerated concrete blocks, coal ash bricks, microporous calcium silicate boards, novel light wall body materials, heat insulating asbestos boards and high-strength gypsum. $CaO—SiO_2—H_2O$ hydrothermal reaction is finished in the autoclave. Moreover, the autoclave system is also widely applicable to rubber product and wood drying and anticorrosion treatment, heavy metal smelting, refractory brick oil impregnation and carburization, composite glass autoclave curing, chemical fiber high-pressure treatment, canned food high temperature and high pressure treatment, paper pulp digestion, cable vulcanization, fishing net shape fixing, and production projects which need a pressure autoclave curing production process in chemical industry, pharmaceutical industry, aerospace industry, heat insulating material industry, textile industry, military industry, etc.

For the autoclave system with the existing structure, the working principle of the steam providing device is a boiler boiling method, i.e., expanded water steam is obtained by heating water to provide the autoclave with steam and pressure. This expansion and pressurization process consumes a great amount of energy.

SUMMARY OF THE INVENTION

The technical problems to be solved by the present invention are problems that energy consumption is great and atmosphere pollution is caused when a boiler boiling method is adopted for providing steam and pressure in an autoclave system.

In order to solve the above-mentioned technical problems, the technical solution adopted by the present invention is to provide a providing method for steam and pressure in a pump-type autoclave system, which comprises the following steps:

an autoclave, a compressor and a water storage container in a steam providing device are connected through a pipeline to form a closed-cycle autoclave system;

the water storage container is heated through a heating device, the water storage container is depressurized by utilizing the compressor to obtain steam and the steam in the water storage container is pressurized and pumped into the autoclave; and the steam in the autoclave acts on materials to be subjected to autoclave curing and is condensed to release heat, and condensate water backflows into the water storage container for cyclic use.

In the above-mentioned method, the internal temperature of the autoclave is adjusted by controlling the proportion of air to steam in fluid which is pumped into the autoclave.

In the above-mentioned method, the internal pressure of the autoclave is adjusted by controlling the flow rate of the fluid which is pumped into the autoclave.

The present invention further provides a pump-type autoclave system, which comprises an autoclave and a steam providing device, wherein said steam providing device comprises a water storage container and a heating device used for heating said water storage device, and said water storage container and said steam autoclave are connected through a pipeline to form a closed loop; and further comprises:

a compressor, wherein an inlet of the compressor is connected with said water storage container, an outlet of the compressor is connected to a steam input port of said autoclave, and a condensate water drain outlet of said autoclave is connected to said water storage container.

In the above-mentioned pump-type autoclave system, a reversing valve is arranged at the inlet of said compressor, a first inlet of said reversing valve is connected with said water storage container through a first pipeline and a second inlet of said reversing valve is connected to the atmosphere.

In the above-mentioned pump-type autoclave system, the outlet of said compressor is connected with a steam inlet of said autoclave through a second pipeline and a flow control valve is arranged on said second pipeline.

In the above-mentioned pump-type autoclave system, energy adopted by said heating device is solar energy, ground source heat, water source heat, air source heat or industrial or living waste heat.

In the above-mentioned pump-type autoclave system, said condensate water drain outlet is connected to a water tank through a third pipeline, the bottom of said water tank is provided with a sewage drain pipe and said water storage container is connected to the upper part of said water tank through a fourth pipeline.

In the above-mentioned pump-type autoclave system, a safety valve is arranged on said autoclave and used for controlling the maximum internal pressure of said autoclave.

In the above-mentioned pump-type autoclave system, a water replenishing pipe is further arranged and used for replenishing water into said water storage container.

The present invention uses the compressor to depressurize an intermediate-low temperature water source to obtain steam, and the steam is pumped into the autoclave and condensed to release heat to obtain corresponding temperature and pressure.

Since the present invention fully utilizes a great amount of low-cost intermediate-low temperature heat sources obtained from natural, industrial or living waste heat to provide needed high temperature, steam and pressure to the autoclave system, the energy is saved.

DESCRIPTION OF THE DRAWING

FIG. 1 is a structural schematic view of a pump-type autoclave system provided by the present invention.

DESCRIPTION OF THE EMBODIMENTS

The present invention provides a pump-type autoclave system and a providing method for steam and pressure thereof. In the technical solution, an autoclave, a compressor and a water storage container in a steam providing device are connected through a pipeline to form a closed loop and further form a closed-cycle system, the water storage container is depressurized by utilizing the compressor to obtain steam and the steam is pressurized and pumped into the autoclave to provide the steam and pressure to the autoclave. Since the present invention fully utilizes a great amount of low-cost intermediate-low temperature heat sources obtained from natural, industrial or living waste heat to provide needed high temperature, steam and pressure to the autoclave system, the energy is saved. The present invention is further described below in details in conjunction with specific embodiments and the drawing.

As shown in FIG. 1, the pump-type autoclave system provided by the present invention comprises an autoclave 10, a steam providing device and a compressor 30, wherein the steam providing device comprises a water storage container 21 and a heating device 22 used for heating the water storage device 21; the autoclave 10, the water storage container 21 and the compressor 30 are connected through a pipeline to form a closed loop system; and the heating device 22 can adopt conventional fuel, electric energy, natural heat such as solar energy, ground source heat, water source heat and air source heat, industrial or living waste heat, etc.

A reversing valve 31 is arranged at the inlet of the compressor 30, an outlet of the reversing valve 31 is connected with the inlet of the compressor 30, a first inlet of the reversing valve 31 is connected with the water storage container 21 through a first pipeline 32, a second inlet of the reversing valve 31 is connected to the atmosphere, the outlet of the compressor 30 is connected with a steam inlet of the autoclave 10 through a second pipeline 33 and a flow control valve 34 is arranged on the second pipeline 33. A temperature sensor 11 and a pressure sensor 22 are arranged in the autoclave 10, the temperature sensor 11 and the pressure sensor 22 continuously detect the internal temperature and the internal pressure of the autoclave 10, and the internal temperature and the internal pressure of the autoclave 10 can be adjusted through the reversing valve 31 and the flow control valve 34 according to the detection signals of the temperature sensor 11 and the pressure sensor 22. The compressor 30 can be optionally communicated with the water storage container 21 or be directly communicated with the atmosphere through the reversing valve 31 to optionally output steam or air into the autoclave 10, and the flow rate of fluid in the second pipeline 34 can be controlled through the flow control valve 34. The condensate water drain outlet of the autoclave 10 is connected to a water tank 40 through a third pipeline 41, the bottom of the water tank 40 is provided with a sewage drain pipe 42, a switching valve 43 is arranged on the sewage drain pipe 42 and the water storage container 21 is connected to the upper part of the water tank 40 through a fourth pipeline 44. The water tank 40 plays a role of settling impurities in condensate water. The present invention is further provided with a water replenishing pipe 23 for replenishing water consumed and lost during equipment operation, and the water replenishing pipe 23 can be arranged on the water storage container 21.

A variable-frequency compressor can also be used as the compressor 30 for controlling the flow and pressure of the fluid.

The working principle of the present invention is as follows:

(1) the water storage container is depressurized by utilizing the compressor, the compressor depressurizing an air pressure in the water storage container in order to reduce a boiling point of water in the water storage container to obtain steam, then the water storage container is heated by the heating device to obtain steam, and since the internal part of the water storage container is in a negative-air-pressure state, the boiling point of water is greatly reduced and the steam can be quickly obtained at lower energy consumption by using the intermediate-low temperature heat source;

(2) the steam is pumped into the autoclave through the compressor, participates in reaction in the autoclave and is condensed to release heat, and heat-containing condensate water backflows into the water storage tank for continuously participating in circulation and continuously releasing heat. Since the condensate water carries a great amount of heat, the amount of energy needed for generating steam is smaller and the energy utilization ratio is high.

Since the present invention fully utilizes a great amount of low-cost intermediate-low temperature heat sources obtained from natural, industrial or living waste heat to provide needed high temperature, steam and pressure to the autoclave system, the energy is saved.

In addition, the present invention provides a complete protection control device, which is specifically described below:

(1) when the internal temperature of the autoclave 10 is lower than a set value, the reversing valve 31 is switched to be communicated with the water storage container 21, steam in the water storage container 21 continuously enters the autoclave 10 and thus the internal temperature of the autoclave 10 is continuously increased;

(2) when the internal temperature of the autoclave 10 is higher than the set value, the reversing valve 31 is switched to be communicated with the atmosphere, the compressor 30 inputs air into the autoclave 10 and does not input the steam any more, and thus the internal temperature of the autoclave 10 is not continuously increased any longer;

(3) when the internal pressure of the autoclave 10 is lower than a set value, the opening of the flow control valve 34 is increased, the air inlet amount of the autoclave 10 is increased and thus the internal pressure of the autoclave 10 is increased; and (4) when the internal pressure of the autoclave 10 is higher than the set value, the opening of the flow control valve 34 is decreased, the air inlet amount of the autoclave 10 is decreased and thus the internal pressure of the autoclave 10 is decreased.

The above-mentioned reversing valve 31 and the flow control valve 34 are automatically controlled through a control unit, i.e., the temperature sensor 11 and the pressure sensor 12 continuously transmit the internal temperature and the internal pressure of the autoclave 10 to the control unit, and the control unit outputs corresponding control signals to the reversing valve 31 and the flow control valve 34 according to the internal temperature and the internal pressure of the autoclave 10.

A pressure reducing valve 13 is further arranged on the autoclave 10. When the internal pressure of the autoclave 10 is accidently and instantaneously increased, the pressure reducing valve 13 is automatically opened to exhaust the steam in the autoclave 10 to guarantee the safe operation of the autoclave 10.

In addition, the pressure reducing valve 13 can also be automatically controlled through the control unit. When the internal temperature or the internal pressure of the autoclave 10 always exceeds the set value within a period of time (such as 2 minutes, which can be set by a user according to actual needs), the control unit gives out a control signal, the pressure reducing valve 13 is opened to exhaust the gaseous steam in the autoclave 10, thus the goal of reducing the internal temperature or the internal pressure of the autoclave 10 is achieved and the safe operation of the autoclave 10 is further guaranteed.

In combination with the introduction of the above-mentioned pump-type autoclave system, the present invention further provides a providing method for steam and pressure in the pump-type autoclave system, which comprises the following steps:

an autoclave, a compressor and a water storage container in a steam providing device are connected through a pipeline to form a closed-cycle autoclave system;

the water storage container is heated through a heating device, the water storage container is depressurized by utilizing the compressor to obtain steam and the steam in the water storage container is pressurized and pumped into the autoclave; and the steam in the autoclave acts on materials to be subjected to autoclave curing and is condensed to release heat, and condensate water backflows into the water storage container for cyclic use.

In the above-mentioned method, the internal temperature of the autoclave is adjusted by controlling the proportion of air to steam in fluid which is pumped into the autoclave; and the internal pressure of the autoclave is adjusted by controlling the flow rate of the fluid which is pumped into the autoclave.

To sum up, the pump-type autoclave system and the providing method for high-temperature steam and pressure thereof provided by the present invention are very practical due to features of low investment, energy conservation, economy and environmental friendliness. Compared with the traditional boiler boiling method, the method has the following prominent advantages:

(1) The precedent of utilizing the internal environment of a heat pump system is creatively started, the internal part of the autoclave is used as a condensing section of the heat pump system, and the temperature and pressure needed by the autoclave are obtained in the internal environment of the heat pump system. In the process, working medium (water/water steam) in the internal environment of the heat pump system is in direct contact with substances (products) to be acted, heat is transferred or chemical reaction happens and thus the efficiency is greatly improved.

(2) The present invention provides a method for obtaining steam and application in the autoclave field. The existing boiler boiling method adopts a process of heating water to obtain expanded water steam to provide the autoclave with steam and pressure, and the expansion and pressurization process consumes a great amount of energy. However, the present invention uses the compressor to depressurize the low temperature water source to obtain steam, which is then pumped into the autoclave and is condensed to release heat to obtain corresponding temperature and pressure. Since a great amount of low-cost intermediate-low temperature heat sources obtained from natural, industrial or living waste heat is fully utilized to provide needed high temperature, steam and pressure to the autoclave system, the energy is saved.

(3) The temperature and pressure provided by adopting the traditional boiler boiling method are complementary to each other, and one condition, i.e., the temperature or the pressure is difficult to quickly and solely adjust. However, by adopting the solution provided by the present invention, any one condition, i.e., the temperature or the pressure can be solely adjusted according to the needs.

The present invention is not limited to the above-mentioned preferable embodiments. It shall be known to any one that, all technical solutions which are identical with or similar to the technical solution of the present invention and are obtained by making structural variations under the inspiration of the present invention, should fall into the protection scope of the present invention.

The invention claimed is:

1. A providing method for steam and pressure in a pump-type autoclave system, comprising the following steps:

connecting an autoclave, a compressor and a water storage container in a steam providing device through a pipeline to form a closed-cycle autoclave system;

heating the water storage container through a heating device, and meanwhile depressurizing an air pressure in the water storage container by utilizing the compressor in order to reduce a boiling point of water in the water storage container to obtain steam, and pumping the steam into the autoclave by the compressor;

enabling the steam in the autoclave to act on materials to be subjected to autoclave curing and condensing the steam to release heat; and enabling condensate water to backflow into the water storage container for cyclic use;

wherein the pipeline includes a first pipeline and a second pipeline, a reversing valve is arranged at an inlet of the compressor, a first inlet of the reversing valve is connected with the water storage container through the first pipeline and a second inlet of the reversing valve is connected to an atmosphere, an outlet of the compressor is connected with a steam inlet of the autoclave through the second pipeline and a flow control valve is arranged on the second pipeline, a temperature sensor and a pressure sensor are arranged in the autoclave, the temperature sensor and the pressure sensor continuously detect an internal temperature and an internal pressure of the autoclave, according to detection signals of the temperature sensor and the pressure sensor, the compressor can be optionally communicated with the water storage container or be directly communicated with the atmosphere through the reversing valve to optionally output steam or air into the autoclave, the internal temperature of the autoclave is adjusted by controlling a proportion of air to steam in fluid which is pumped into the autoclave; the internal pressure of the autoclave is adjusted by the flow rate of fluid in the second pipeline through the flow control valve.

* * * * *